US006231865B1

(12) United States Patent
Hsu et al.

(10) Patent No.: US 6,231,865 B1
(45) Date of Patent: May 15, 2001

(54) NATURAL PESTICIDE

(75) Inventors: Hsinhung John Hsu; Jian Zhou; Chun-Hua Lily Chang, all of Ventura, CA (US)

(73) Assignee: Safer Gro Laboratories, Inc., Ventura, CA (US)

( * ) Notice: Subject to any disclaimer, the term of this patent is extended or adjusted under 35 U.S.C. 154(b) by 0 days.

(21) Appl. No.: 09/273,636

(22) Filed: Mar. 23, 1999

Related U.S. Application Data
(60) Provisional application No. 60/079,505, filed on Mar. 26, 1998.

(51) Int. Cl.$^7$ .................................................... A01N 65/00
(52) U.S. Cl. ......................................... 424/195.1; 424/405
(58) Field of Search ................................ 424/195.1, 405

(56) References Cited

U.S. PATENT DOCUMENTS

| | | |
|---|---|---|
| 4,455,304 | 6/1984 | Yaralian . |
| 4,876,090 | 10/1989 | Weisler . |
| 5,227,162 | 7/1993 | Ferrari . |
| 5,417,973 | 5/1995 | King . |
| 5,468,493 | 11/1995 | Funkunaga . |
| 5,645,845 | 7/1997 | Neumann . |
| 5,711,953 | 1/1998 | Bassett . |

FOREIGN PATENT DOCUMENTS

| | | |
|---|---|---|
| 1 074 751 | 7/1967 | (GB) . |

OTHER PUBLICATIONS

Computer JPAB Abstract JP–10130114 Sugiyama et al May 19, 1998.*
Computer Derwent CRUPU Abstract 199–88467 Doghairi et al "Evaluation of various repellents for control of flea beetle on broccoli, 1996" Arthropod Manage. Tests (22, 85, 1997) 1 Tab.*
Garlic Barrier Ag, Allium S. E.,,May 26, 1996, pp. 1,3., online—http://www.cyberstreet.com/garlic/gar_bar.htm :2 pages.
V. Frantz, "Insect pest control in the greenhouse: alternatives to commercial toxins", Proceedings of the Indiana Academy of Science, (1984) vol. 94, pp. 98: 1 page. XP002107681.
N. Montoyama, et al, "Insecticidally active component of the so–called natural plant–extract formulation 'Muso'; used as organic agricultural materials", J. Pestice.Sci. (21, No. 1, 73–79, 1996): 1 page. XP002107682.
H.M. Flint, et al, "Test of garlic oil for the control of the silverleaf whitefly, Bemesia argentifolii bellows and perring (Homoptera: Aleyrodidae) in cotton", The Southwestern Entomologist (vol. 20, No. 2, 1995, pp. 137–150): 9 pages.
D. L.Kerns, et al, "Control of lepidopterous larvae on lettuce with garlic, 1996", Anthropod Manage. Tests (22, 135, 1997, p.135): 1 page.

T. H. Brigs et al, "Organic Insecticides not used as effective as synthetics, but still useful for vegetable insect control", Highlights of Agricultural Research—Alabama Agriculteral Experiment Station, (1996) vol. 43, No. 3, pp. 16–18: 1 page. XP–002107685.

Jiang C. et al, Pure mashed odour–free garlic, CN 1 123 624 A, Derwent Publications Ltd., Jun. 5, 1996: 1 page. XP–002107687.

Zhang Y., Multi–flavour nutritious garlic sauce, CN 1 128 107 A, Derwent Publications Ltd., Aug. 7, 1996: 1 page. XP–002107688.

Jiang C. et al, Garlic Chilli Sauce, CN 1 119 498 A, Derwent Publications Ltd., Apr. 3, 1996: 1 page. XP–002107689.

Nippon Seiyaku KK, Plant disease and insect pest inhibitor, useful as agricultural material—contains at least on of ougon, clove, garlic, kouboku or soujutu, JP9067220 A 970311, Derwent Publications Ltd., Mar. 11, 1997: 1 page. XP–002107690.

Montes Belmont R., et al, "Control of Aspergillus flavus in maize with plant essential oils and their components", J. Food Prot. (61, No. 5, 616–19. 1998), Derwent Publications Ltd.: 1 page. XP–002107686.

G. Prasad and V. D. Sharma Antifungal Property of Garlic (Allium satiuum Linn.) in Poultry Feed Substrate.

Gary S. Moore and Robin D. Atkins The Fungicidal and Fungistatic Effects of an Aqueous Garlic Extract on Medically Important Yeast–like Fungi.

Chester J. Cavallito and John Hays Bailey Allicin, The Antibacterial Principle of Allium satiuum. I. Isolation, Physical Properties and Antibacterial Action.

Chester, J. Cavallito, John Hays Bailey and Johannes S. Buck The Antibacterial Principle of Allium satiuum. III IB Precursor and "Essential Oil of Garlic".

* cited by examiner

Primary Examiner—Herbert J. Lilling

(57) ABSTRACT

The invention describes a synergistic effect when garlic oil or extract is combined with essential oils which results in an improved insecticide/fungicide which is natural and contains no chemical additives. Essential oils are defined in this application to be volatile liquids obtained from plants and seeds including cotton seed oil, soybean oil, cinnamon oil, corn oil, cedar oil, castor oil, clove oil, geranium oil, lemongrass oil, linseed oil, mint oil, sesame oil, thyme oil, rosemary oil, anise oil basil oil, camphor oil, citronella oil, eucalyptus oil, fennel oil, ginger oil, grapefruit oil, lemon oil, mandarin oil, orange oil, pine needle oil, pepper oil, rose oil, tangerine oil, tea tree oil, tee seed oil, mineral oil and fish oil.

5 Claims, No Drawings

NATURAL PESTICIDE

This application claims priority of United States provisional application bearing Ser. No. 60/079,505 filed Mar. 26, 1998.

BACKGROUND

This invention relates to a composition of matter used as a natural pesticide and a method for inhibiting the growth of bacteria, fungi and insect pests.

Garlic (*Allium sativum* Linn.) and/or its extract have been reported to have antibacterial and/or antifungal properties. It is known that Allicin isolated from the cloves of garlic had antibacterial properties against both Gram positive and Gram negative bacteria. Further, aqueous extracts of garlic have been reported to inhibit the growth of a variety of yeast-like fungi in the genera Candida, Cryptococcus, Rhudotoruto, Torulopsis and Trichosporon. It has also been previously reported that garlic extract and chips inhibit the growth of fungi such as *Candida albicans, Aspergillus fumigatus* and *Aspergillus parasiticus*. Because of its anti-fungal and antibacterial properties, garlic or its extract have been used as pesticides to control plant diseases such as mildew. It has also been used as an insecticide to control plant insects such as army worms, aphids and Colorado beetles. Most recently, a method used to repel mosquitos using garlic extract and water was granted U.S. Pat. No. 5,733,552 issued to Anderson et. al.

SUMMARY

The present invention is directed to a composition of matter which comprises garlic extract and essential oils. This combination of natural ingredients, when applied to plants, has superior anti-fungal and anti-bacterial qualities, than if applied separately.

A combination of garlic extract and essential oil has a synergistic effect which significantly increases the effectiveness of garlic and/or garlic extract. The ideal ratio of garlic to essential oil is 10–70% garlic extract to 90–30% essential oil. However, a ratio of 5–98% garlic extract to 95–2% essential oil can be used.

Garlic extract can be obtained by the blending and mixing of garlic cloves with water, oil or organic solvents. The mixture is then filtered to obtain garlic extract.

Definitions

Essential Oil is defined as a subtle, volatile liquid obtained from plants and seeds, including but not limited to cotton seed oil, soybean oil, cinnamon oil, corn oil, cedar oil, castor oil, clove oil, geranium oil, lemongrass oil, linseed oil, mint oil, sesame oil, thyme oil, rosemary oil, anise oil, basil oil, camphor oil, citronella oil, eucalyptus oil, fennel oil, ginger oil, grapefruit oil, lemon oil, mandarin oil, orange oil, pine needle oil, pepper oil, rose oil, tangerine oil, tea tree oil and tea seed oil.

Garlic extract is defined as any liquid removed from cloves of garlic and may therefore include garlic oil and water. Garlic extract has the same meaning as garlic juice.

Disease index represents the severity of the disease present on a plant. This is a subjective assessment and is categorized in the following manner:

| Scale | % Infection |
|---|---|
| 0 | 0 |
| 1 | 1–10 |
| 2 | 11–20 |
| 3 | 21–50 |
| 4 | 51–100 |

The disease index is calculated by the following formula:

$$DI = \frac{[(S_0 L_0) + (S_1 L_1) + (S_2 L_2) + (S_3 L_3) + (S_4 L_4)]}{L_{total} \times 4} \times 100$$

Where DI=Disease index
S=Scale category 0, 1, 2, 3 or 4)
L=number of leaves per scale category The degree of control represents the efficiency of the product in controlling the disease and is calculated by the following formula:

$$DC = \frac{DI_{non\text{-}treated\ area} - DI_{treated\ area}}{DI_{non\text{-}treated\ area}} \times 100$$

A degree of control of 0 represents no control and 100 represents total control of the disease.

DETAILED DESCRIPTION

Preparation of Garlic Extract

Garlic extract was prepared by thoroughly mixing two thousand grams of garlic cloves with 4,000 grams of water in a blender. The mixture was then filtered with the filtrate collected as garlic extract.

Samples 1–4

Samples 1–4 were mixed as indicated in the following chart at ambient conditions:

| Composition of Samples 1–4 (all values in grams) | | | | |
|---|---|---|---|---|
| | Sample 1 | Sample 2 | Sample 3 | Sample 4 |
| Garlic Extract | 600 | 850 | 600 | 600 |
| Cotton Seed Oil | 300 | — | 250 | — |
| Cinnamon Oil | — | 50 | 50 | — |
| Mineral Oil | — | — | — | 300 |
| Soduim Lauryl Sulfate | 100 | 100 | 100 | 100 |

Sodium Lauryl Sulfate is used to emulsify the garlic extract with either an essential oil or mineral oil.

Experiments

Experiment A—Powdery Mildew Disease on Cucumber Plants

Cucumber plants were grown for 14 days in a greenhouse. The leaves were then inoculated with a spore suspension of powdery mildew disease. Three weeks after the spore inoculation, all cucumber plants developed powdery mildew disease. Fifteen cucumber plants were selected for testing. The plants were randomly assigned into 5 groups having 3 plants per group. Five spray compositions were prepared. Each of the following, Sample 1, Garlic Extract, Cotton Seed Oil and Sodium Lauryl Sulfate were diluted one part to 49 parts water. The fifth spray composition was water.

Each group of plants then received one of the above-mentioned compositions by foliar spray treatment twice with a 7 day interval between each treatment. The spray treatments consisted of totally wetting the plant leaves.

Seven days after the second application, the plants were examined for powdery mildew disease. The disease indices were recorded to show the severity of the disease and are reported below:

Test Results 7 Days after Second Spray Application

|  | Disease Index | Degree of Control |
|---|---|---|
| Sample 1 | 1.3 | 97.2% |
| Garlic Extract | 5.0 | 89.4% |
| Cotton Seed Oil | 8.0 | 83.1% |
| Sodium Lauryl Sulfate | 31.8 | 32.6% |
| Water | 47.2 | 0.0% |

The results indicate that garlic extract in combination with cotton seed oil (sample 1) is better than garlic extract or cotton seed oil alone on controlling powdery mildew disease on cucumber plants.

Experiment B—Powdery Mildew Disease on Cucumber Plants

The testing in Experiment A was repeated with 28 cucumber plants divided into 7 groups (Groups 6–12), each group having 4 plants. Seven spray compositions were prepared. Each of the following: Sample 1, Sample 2, Garlic Extract, Cotton Seed Oil, Cinnamon Oil and Sodium Lauryl Sulfate, were diluted one part to 99 parts water. The seventh spray composition was water. The seven groups received the foliar spray treatments twice with a 7 day interval between each treatment.

Three days after each application, the plants were examined for powdery mildew disease. The disease indices were recorded to show the severity of the disease and are reported as follows:

Test Results 3 Days after Application

|  | 1st Application | | 2nd Application | |
|---|---|---|---|---|
|  | Disease Index | Degree of Control | Disease Index | Degree of Control |
| Sample 1 | 14.6 | 77.4% | 10.0 | 81.3% |
| Sample 2 | 12.5 | 80.6% | 6.7 | 87.5% |
| Garlic Extract | 27.1 | 58.2% | 20.0 | 62.5% |
| Cotton Seed Oil | 56.3 | 12.9% | 43.3 | 18.8% |
| Cinnamon Oil | 56.3 | 12.9% | 50.0 | 6.2% |
| Sodium Lauryl Sulfate | 60.4 | 6.4% | 51.7 | 3.1% |
| Water | 64.4 | 0.0% | 53.3 | 0.0% |

The results indicate that the combination of garlic extract and either cottonseed oil (sample 1) or cinnamon oil (sample 2) inhibit the growth of powdery mildew disease more effectively than applications not in combination.

Experiment C—Powdery Mildew Disease on Cucumber Plants

The testing in Experiment B was repeated; this time with each foliar spray application diluted with 199 parts water instead of 99 parts water.

Three days after each application, the plants were examined for powdery mildew disease. The disease indices were recorded to show the severity of the disease and are reported as follows:

Test Results 3 Days after Application

|  | 1st Application | | 2nd Application | |
|---|---|---|---|---|
|  | Disease Index | Degree of Control | Disease Index | Degree of Control |
| Sample 1 | 25.0 | 61.3% | 20.0 | 62.5% |
| Sample 2 | 25.0 | 61.3% | 25.0 | 53.1% |
| Garlic Extract | 33.3 | 48.6% | 26.7 | 50.0% |
| Cotton Seed Oil | 60.4 | 6.5% | 45.0 | 15.6% |
| Cinnamon Oil | 56.3 | 12.9% | 51.7 | 3.1% |
| Sodium Lauryl Sulfate | 62.5 | 3.2% | 51.7 | 3.1% |
| Water | 64.6 | 0.0% | 53.3 | 0.0% |

The results indicate that the combination of garlic extract and either cottonseed oil (sample 1) or cinnamon oil (sample 2) inhibit the growth of powdery mildew disease more effectively than either garlic extract, cottonseed oil or cinnamon oil separately. The increased dilution of each spray composition with water did reduce the effectiveness of controlling powdery mildew disease.

Experiment D—Powdery Mildew Disease on Red Rose Plants

Red rose plants were grown in a greenhouse having powdery mildew disease. In order to test the effectiveness of the combination of garlic extract and cottonseed oil (sample 1) on controlling the disease, the plants were sprayed once with a solution consisting of sample 1 diluted with 50 times water. The control plants were sprayed with water only. The plants were investigated 10 days after the spray application.

The Effectiveness of Sample 1 on Controlling Powdery Mildew Disease on Red Rose Plants

|  | Disease Index | Degree of Control |
|---|---|---|
| Sample 1 | 15 | 66.7% |
| Garlic Extract | 20 | 55.6% |
| Cotton Seed Oil | 25 | 44.4% |
| Water Only | 45 | 0.0% |

Sample 1, a combination of garlic extract and cotton seed oil diluted with 50 times water, was more effective on controlling powdery mildew disease on red rose plants than garlic extract or cotton seed oil individually.

Experiment E—Powdery Mildew Disease on Yellow Rose Plants

Example D was repeated using yellow rose plants for test and the plants were sprayed with sample 1 diluted with 50 times water, three times at 1 week intervals. The control plants were sprayed with water only. The plants were investigated 10 days after each spray application.

Test Results 10 Days after Application for Controlling Powdery Mildew Disease on Yellow Rose Plants

|  | 1st Application | | 2nd Application | | 3rd Application | |
|---|---|---|---|---|---|---|
|  | Disease Index | Degree of Control | Disease Index | Degree of Control | Disease Index | Degree of Control |
| Sample 1 | 70 | 30% | 55 | 45% | 15 | 75% |
| Garlic extract | 80 | 20% | 70 | 30% | 40 | 60% |

-continued

Test Results 10 Days after Application for Controlling Powdery Mildew Disease on Yellow Rose Plants

|  | 1st Application | | 2nd Application | | 3rd Application | |
|---|---|---|---|---|---|---|
|  | Disease Index | Degree of Control | Disease Index | Degree of Control | Disease Index | Degree of Control |
| Cottonseed oil | 85 | 15% | 75 | 25% | 45 | 55% |
| Water Only | 100 | 0% | 100 | 0% | 100 | 0% |

Sample 1, a combination of garlic extract and cotton seed oil, when diluted with 50 times water, was more effective on controlling powdery mildew disease on yellow rose plants than garlic extract or cottonseed oil individually.

Experiment F—Powdery Mildew Disease on White Rose Plants

Example D was repeated using white rose plants for test and the plants were sprayed with sample 1 diluted with 50 times water, twice with a 1 week interval. The control plants were sprayed with water only. The plants were investigated 10 days after both spray applications.

Test Results 10 Days after Application for Controlling Powdery Mildew Disease on White Rose Plants

|  | 1st Application | | 2nd Application | |
|---|---|---|---|---|
|  | Disease Index | Degree of Control | Disease Index | Degree of Control |
| Sample 1 | 55 | 38.9% | 5 | 87.5% |
| Garlic Extract | 65 | 27.8% | 20 | 50.0% |
| Vegetable Oil | 75 | 16.7% | 25 | 37.5% |
| Water Only | 90 | 0.0% | 40 | 0.0% |

Sample 1, a combination of garlic extract and cotton seed oil, when diluted with 50 times water, was more effective on controlling powdery mildew disease on white rose plants than either garlic extract or vegetable oil individually.

Experiment G—Powdery Mildew Disease on Cucumber Plants

Eight cucumber plants with powdery mildew disease were randomly divided into 2 groups having 4 plants each. One group was sprayed with Sample 1 diluted with 49 parts water. The other group of cucumber plants is designated the control group and is only sprayed with water. Both groups of plants were sprayed twice with an interval of 11 days. The disease indices before and after the treatments and the degrees of control are shown below:

The Effectiveness of Sample 1 on Controlling Powdery Mildew Disease on Cucumber Plants

|  | Disease Index Before Application | 1st Application | | | | 2nd Application | | | |
|---|---|---|---|---|---|---|---|---|---|
|  |  | 3 Days | | 6 Days | | 11 Days | | 21 Days | |
|  |  | Disease Index | Degree of Control | Disease Index | Degree of Control | Disease Index | Degree of Control | Disease Index | Degree of Control |
| Sample 1 | 38.8 | 0 | 100% | 0 | 100% | 17.5 | 70% | 18.8 | 74% |
| Water only | 35.0 | 35.0 | 0% | 46.3 | 0% | 57.5 | 0% | 73.2 | 0% |

Experiment H—Control of White Fly on Cucumber Plants

Sample 1, diluted with 50 times water, was tested for the control of white fly on cucumber plants. The leaves of cucumber plants were sprayed while adult white flies present, and the mortality rate was tested as follows:

Effectiveness of Sample 2 on Controlling White Fly

| Test No. | White Flies (before spraying) | White Flies Dead (after spraying) | Mortality (%) |
|---|---|---|---|
| 1 | 124 | 84 | 67.7 |
| 2 | 74 | 51 | 68.9 |
| 3 | 113 | 62 | 54.8 |
| 4 | 187 | 117 | 62.6 |

Experiment I—Control of Red Spider Mites on Bush Bean Plants

Samples 1, 2, 3, and 4 were used to test the control of red spider mites on bush bean plants. The samples, as well as solutions of garlic extract, cotton seed oil, cinnamon oil, and mineral oil were diluted with 100 times water and sprayed on to bush bean plants which had red spider mites grown on the leaves. The mortality of red spider mites was determined as a percentage in two tests with the results as follows:

Effectiveness Comparison on Red Spider Mites

| Solution (diluted w/100 times water) | Test 1 Mortality (%) | Test 2 Mortality (%) |
|---|---|---|
| Sample 1 | 84 | 86 |
| Sample 2 | 88 | 93 |
| Sample 3 | 81 | 84 |

Effectiveness Comparison on Red Spider Mites

| Solution (diluted w/100 times water) | Test 1 Mortality (%) | Test 2 Mortality (%) |
| --- | --- | --- |
| Sample 4 | 68 | 72 |
| Garlic Extract | 53 | 58 |
| Cotton Seed Oil | 49 | 61 |
| Cinnamon Oil | 59 | 64 |
| Mineral Oil | 15 | 28 |
| Water | 2 | 8 |

Samples 1, 2, and 3 which contain a combination of garlic extract and an essential oil, were more effective in eradication of red spider mites than using garlic extract, essential oil, or mineral oil separately, or using a combination of garlic extract and mineral oil (sample 4).

Experiment J—Control of Two Spotted Spider Mites on Bush Bean Plants

Samples 1, 2, 3, and 4 were used to test the control of two spotted spider mites on bush bean plants. The samples as in Experiment I above, were diluted with 100 times water and sprayed on to bush bean plants which had two spotted spider mites grown on the leaves. The mortality of two spotted spider mites was determined as a percentage in two tests with the results as follows:

Effectiveness Comparison on Two Spotted Spider Mites

| Solution (diluted w/100 times water) | Test 1 Mortality (%) | Test 2 Mortality (%) |
| --- | --- | --- |
| Sample 1 | 78 | 82 |
| Sample 2 | 84 | 91 |
| Sample 3 | 76 | 89 |
| Sample 4 | 65 | 71 |
| Garlic Extract | 53 | 48 |
| Cotton Seed Oil | 36 | 42 |
| Cinnamon Oil | 56 | 61 |
| Mineral Oil | 13 | 21 |
| Water | 5 | 7 |

Samples 1, 2, and 3 which contain a combination of garlic extract and an essential oil, were more effective in eradication of two spotted spider mites than using garlic extract, essential oil, or mineral oil separately, or using a combination of garlic extract and mineral oil (sample 4).

The following experiments relate to suppressing fungal growth (Experiment K) and suppressing fungal germination (Experiment L).

Experiment K—Suppression of Rhizoctonia sp., Trichoderma sp., and Botrytis sp.

Sample 1 was laboratory tested for the suppression of different fungi. Sample 1 was added to PDA (Potato Dextrose Agar) growth medium solution at the Sample 1:PDA solution ratio between 1:100 and 1:3200. The solutions were then poured into test tubes and inoculated with one of the three different fungi; Rhizoctonia sp., Trichoderma sp., and Botrytis sp. The test tubes were then incubated at 25 C for 14 days. The growth of the fungi in different treatments were recorded and shown in the following table.

Growth of Three Different Fungi in PDA Solution with Different Concentrations of Sample 1.

| Fungi | 0 | 1/100 | 1/200 | 1/400 | 1/800 | 1/1600 | 1/3200 |
| --- | --- | --- | --- | --- | --- | --- | --- |
| Rhizoctonia sp. | ++ | + | ++ | ++ | ++ | ++ | ++ |
| Trichoderma sp. | ++ | − | + | + | + | + | + |
| Botrytis sp. | ++ | + | + | + | + | + | + |

Legend:
++ Normal Growth
+ Reduced Growth
− No Growth

The test results indicate at the Sample 1:PDA ratio of 1:100, Sample 1 suppressed the growth of all fungi tested. However, at weaker concentrations 1:200–1:3200, Sample 1 suppressed the growth of both Trichoderma sp. and Botrytis sp. but not Rhizoctonia sp.

Experiment L—Suppression of Penicillium sp. Botrytis sp. and Aspergillus sp. spore germination Samples 1, 2, 3, and 4 were tested in the laboratory for the suppression on the germination of spores from 3 different fungi: Penicillium sp. Botrytis sp. and Aspergillus sp. Spore suspensions were prepared and inoculated onto PDA plates. After the inoculation, 1 ml of 1/50 solution of Samples 1, 2, 3, and 4 were added to respective plates receiving the treatment and the plates were horizontally shaken to distribute the solution evenly over the PDA surface. Two sets of control plates were prepared by adding either water or water plus sodium lauryl sulfate solution to the inoculated plates. The plates were then incubated at 26 C for 18–20 hours and then examined under a microscope for evidence of spore germination. The number of germinated and ungerminated spores and the percentage of germination are shown in the following table.

Germination of Spores

| | Penicillium sp. | | | Botrytis sp. | | | Aspergillus sp. | | |
| --- | --- | --- | --- | --- | --- | --- | --- | --- | --- |
| | # Germinated | # Un-Germinated | % Germinated | # Germinated | # un-Germinated | % Germinated | # Germinated | # un-Germinated | % Germinated |
| Sample 1 | 0 | 150 | 0 | 0 | 150 | 0 | 0 | 150 | 0 |
| Sample 2 | 0 | 150 | 0 | 0 | 150 | 0 | 0 | 150 | 0 |
| Sample 3 | 0 | 150 | 0 | 0 | 150 | 0 | 0 | 150 | 0 |
| Sample 4 | 3 | 147 | 2.0 | 0 | 150 | 0 | 0 | 150 | 0 |

-continued

| | Germination of Spores | | | | | | | | |
|---|---|---|---|---|---|---|---|---|---|
| | Penicillium sp. | | | Botrytis sp. | | | Aspergillus sp. | | |
| | # Germinated | # Un-Germinated | % Germinated | # Germinated | # un-Germinated | % Germinated | # Germinated | # un-Germinated | % Germinated |
| Water + SLS | 138 | 12 | 92.0 | 146 | 4 | 97.3 | 132 | 18 | 88.0 |
| Water Only | 135 | 15 | 90 | 144 | 6 | 96.0 | 130 | 20 | 86.7 |

All samples tested totally suppressed the germination of spores of the three tested fungi with the exception of Sample 4 on Penicillium sp.

What is claimed is:

1. A concentrated natural insecticide for inhibiting the growth of insects comprising:

(A) garlic extract;
   (B) oil selected from the group consisting of cotton seed oil, and cinnamon oil;
   the volume ratio of garlic extract to said oil is between 5%–98% garlic extract to 95%–2% oil; and,
   when said concentrated natural insecticide is diluted with water, the combination of said (A) and (B) is a more effective insecticide than if an equivalent amount of either said (A) or said (B) were used alone.

2. A concentrated natural pesticide comprising:

(A) garlic extract;
   (B) oil selected from the group consisting of cotton seed oil, and cinnamon oil;
   the volume ratio of garlic extract to said oil is between 5%–98% garlic extract to 95%–2% oil; and,
   when said concentrated natural pesticide is diluted with water, the combination of said (A) and (B) is more effective for inhibiting the growth of powdery mildew disease than if an equivalent amount of either said (A) or said (B) were used alone.

3. A concentrated natural fungicide comprising:

(A) garlic extract;
   (B) oil selected from the group consisting of cotton seed oil, and cinnamon oil;
   the volume ratio of garlic extract to said oil is between 5%–98% garlic extract to 95%–2% oil; and,
   when said concentrated natural fungicide is diluted with water, the combination of said (A) and (B) is more effective for inhibiting the growth of Rhizoctonia sp., Trichoderma sp., and Botrytis sp. than if an equivalent amount of either said (A) or said (B) were used alone.

4. A concentrated natural pesticide comprising:

(A) garlic extract;
   (B) oil selected from the group consisting of cotton seed oil, and cinnamon oil;
   the volume ratio of garlic extract to said oil is between 5%–98% garlic extract to 95%–2% oil; and,
   when said concentrated natural pesticide is diluted with water, the combination of said (A) and (B) is a more effective pesticide than if an equivalent amount of either said (A) or said (B) were used alone.

5. A concentrated natural fungicide comprising:

(A) garlic extract;
   (B) oil selected from the group consisting of cotton seed oil, and cinnamon oil;
   the volume ratio of garlic extract to said oil is between 5%–98% garlic extract to 95%–2% oil; and,
   when said concentrated natural pesticide is diluted with water, the combination of said (A) and (B) is a more effective fungicide than if an equivalent amount of either said (A) or said (B) were used alone.

* * * * *